(12) United States Patent
Wilson

(10) Patent No.: US 11,585,809 B2
(45) Date of Patent: Feb. 21, 2023

(54) NANOBEAD CONTAINING BIOSENSORS AND METHODS OF PRODUCTION AND USE THEREOF

(71) Applicant: Siemens Healthcare Diagnostics Inc., Tarrytown, NY (US)

(72) Inventor: Michael S. Wilson, Waltham, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 805 days.

(21) Appl. No.: 16/486,926

(22) PCT Filed: Feb. 28, 2018

(86) PCT No.: PCT/US2018/020136
§ 371 (c)(1),
(2) Date: Aug. 19, 2019

(87) PCT Pub. No.: WO2018/160644
PCT Pub. Date: Sep. 7, 2018

(65) Prior Publication Data
US 2021/0132056 A1    May 6, 2021

Related U.S. Application Data

(60) Provisional application No. 62/466,741, filed on Mar. 3, 2017.

(51) Int. Cl.
*G01N 27/327*    (2006.01)
*G01N 33/543*    (2006.01)
*G01N 27/333*    (2006.01)

(52) U.S. Cl.
CPC ... *G01N 33/54386* (2013.01); *G01N 27/3278* (2013.01); *G01N 27/333* (2013.01); *G01N 33/54346* (2013.01)

(58) Field of Classification Search
CPC ....... G01N 33/54386; G01N 33/54346; G01N 27/3278; G01N 27/333; G01N 27/327–3272; C12Q 1/001
See application file for complete search history.

(56) References Cited

U.S. PATENT DOCUMENTS

| | | | | |
|---|---|---|---|---|
| 4,225,410 | A | * | 9/1980 | Pace ............... G01N 33/492 435/817 |
| 5,310,469 | A | * | 5/1994 | Cunningham ......... C12Q 1/001 204/414 |

(Continued)

FOREIGN PATENT DOCUMENTS

| | | | | |
|---|---|---|---|---|
| CN | 1340704 | A | * | 3/2002 ............. G01N 27/30 |
| CN | 202916237 | U | | 5/2013 |

(Continued)

OTHER PUBLICATIONS

Mishra et al., "Immobilization of urease in alginate beads for urea estimation," Research 2015:2:1328. Downloaded on Jun. 23, 2022 from http://www.research-journal.net/en/Immobilization-of-urease-in-alginate-beads-for-urea-estimation.html. The artice is seven pages long, not unmbered. (Year: 2015).*

(Continued)

*Primary Examiner* — Alexander S Noguerola

(57) ABSTRACT

Multi-use biosensors are disclosed that include enzymes coupled to nanobeads; the multi-use biosensors are used to detect analytes in fluidic biological samples, and the biosensors also maintain their enzyme activity after many uses. Multi-sensor arrays are disclosed that include multiple biosensors. Also disclosed are methods of producing and using these devices.

27 Claims, 5 Drawing Sheets

(56) References Cited

U.S. PATENT DOCUMENTS

| | | | |
|---|---|---|---|
| 5,476,776 A | | 12/1995 | Wilkins |
| 5,696,314 A | | 12/1997 | McCaffrey et al. |
| 6,627,057 B1 | * | 9/2003 | Bhullar .............. G01N 27/3272 |
| | | | 204/403.01 |
| 6,982,027 B2 | * | 1/2006 | Yagi ....................... C12Q 1/001 |
| | | | 204/403.05 |
| 7,959,791 B2 | | 6/2011 | Kjaer et al. |
| 2006/0194263 A1 | | 8/2006 | Boussaad et al. |
| 2009/0071846 A1 | | 3/2009 | Staib et al. |
| 2011/0139617 A1 | * | 6/2011 | Fransaer ................ C25D 13/04 |
| | | | 204/477 |
| 2011/0286888 A1 | | 11/2011 | Barlag |
| 2014/0026646 A1 | | 1/2014 | Feldman et al. |
| 2015/0082874 A1 | | 3/2015 | Samproni et al. |
| 2015/0112175 A1 | | 4/2015 | Yao et al. |

FOREIGN PATENT DOCUMENTS

| | | | |
|---|---|---|---|
| EP | 0247850 A1 | | 12/1987 |
| EP | 0318452 A1 | | 5/1989 |
| EP | 0771867 A2 | | 5/1997 |
| EP | 1376115 A2 * | 1/2004 | ............ G01N 27/403 |
| JP | S5843797 A | | 3/1983 |
| JP | H03160358 A | | 7/1991 |
| JP | H08193969 A | | 7/1996 |
| JP | 2009031283 A | | 2/2009 |
| JP | 2013220066 A | | 10/2013 |
| JP | 2015508902 A | | 3/2015 |
| KR | 20160100423 A | | 8/2016 |
| WO | 9914315 A1 | | 3/1999 |
| WO | 2015155665 A1 | | 10/2015 |

OTHER PUBLICATIONS

EPO computer-generated English language translation of CN 1340704 A, patent published Mar. 20, 2002 (Year: 2002).*

Cernat et al., "Micro—to nanostrucured poly (pyrrole-nitrilotriacetic acid) films via nanosphere templates: applications to 3D enzyme attachment by affinity interactions", 2014, Analytical and Bioanalytical Chemistry, 406, pp. 1141-1147.

International Search Report and Written Opinion of International Application No. PCT/US2018/020136 dated May 25, 2018.

European Search Report and Search Opinion of European Application No. 18761276.7 dated Feb. 11, 2020.

Gil et al., "Covalent binding of urease on ammonium-selective potentiometric membranes", 1992, Biosensors & Bielectronics, vol. 7, Issue 9, pp. 645-652.

Maaref et al., "Comparative study between organic and inorganic entrapment matrices for urease biosensor development", Nov. 15, 2006, Sensors and Actuators B, vol. 123, pp. 671-679.

Puech et al., "New polymer and latex prepared by vinyl polymerization of derivatives of norbomene catalyzed by PdCl2, or PdCl2(TPPTS)2 in water", Jun. 30, 2000, Colloids and Surfaces A: Physicochemical and Engineering Aspects, vol. 167, pp. 123-130.

Butt et al., "Enzyme Urea Biosensor Based on a Modified Potentiometric PVC-Nonactin Membrane Electrode for Assay of Urea in Blood", Apr. 13, 1992, Analytical Letters, 25(9), pp. 1597-1615.

* cited by examiner

NANOBEAD CONTAINING BIOSENSORS AND METHODS OF PRODUCTION AND USE THEREOF

CROSS REFERENCE TO RELATED APPLICATIONS/INCORPORATION BY REFERENCE STATEMENT

This application claims priority to U.S. Provisional Application No. 62/466,741, filed Mar. 3, 2017, the disclosure of which is hereby incorporated by reference in its entirety.

STATEMENT REGARDING FEDERALLY SPONSORED RESEARCH OR DEVELOPMENT

Not Applicable.

BACKGROUND

A sensor, also called a detector, is a device that measures a physical quantity and converts it to a signal which may be read by an observer or by an instrument. Sensors are used in chemical and biochemical testing to determine characteristics of an analyte of interest within a specimen or sample. In biomedicine and biotechnology, sensors which detect analytes having a biological component, such as cells, protein, or nucleic acid, are referred to as biosensors.

Biosensor arrays, in which multiple biosensors are grouped into a single unit, are useful in chemistry and medicine to determine the presence and/or concentration of a biological analyte. For example, various types of analytical tests related to patient diagnosis and therapy can be performed by analysis of a liquid sample taken from a patient. Bodily fluids commonly tested include urine, blood, plasma, saliva, cerebrospinal fluid, pleural fluid, and the like. Blood samples, for example, are routinely analyzed to obtain measurements of the partial pressures of $CO_2$ and $O_2$ and concentrations of electrolytes and metabolites in the blood. To determine the presence and concentrations of biological analytes, biosensors are generally used which include immobilized enzymes to attract and capture the analytes. Specifically, potentiometric biosensors are often employed which can utilize an ion-selective electrode or an electrode having an ion-permeable membrane that selectively permits the ion of interest to diffuse through. The operating principle is based on the measureable potential difference that is created when an ion equilibrates between two phases.

A number of different analyzers currently exist for making such measurements utilizing rigid layered sensor assemblies and electrical circuits. Such sensor assemblies are used to assess the condition of medical patients through primary clinical indications. Because of the frequency with which many patients are tested, the ability to use small sample sizes for performing analysis is desirable. Patients in intensive care units may require a sampling frequency of 15-20 per day for blood gas and clinical chemistry measurements. In these cases, analyzing small blood samples is desirable, due to the relatively large number of samples taken in a relatively short period of time. Further, to limit the number of tests performed, it is desirable to gather as much information as possible with each test.

Currently, single-use biosensors and multi-use biosensors are available for use in sensor arrays, such as the sensor arrays set forth in U.S. Publication Nos. 2015/0082874 and 2011/0286888 and International Publication No. WO 2015/155665 (the entire contents of each of which are hereby expressly incorporated herein by reference). One example of an assay amenable to biosensor measurement is the Blood Urea Nitrogen (BUN) assay. The BUN assay measures the amount of nitrogen in blood from the waste product, urea. Urea is a byproduct produced by the kidneys when protein is broken down. While urea is produced in the liver, it passes through the kidneys, and measuring BUN allows medical and clinical practitioners to assess the renal function of patients. Higher than normal BUN levels indicate that a patient's kidneys are not functioning properly. Single-use BUN biosensors are currently available; said biosensors use a range of urease immobilization methods such as glutaraldehyde crosslinking (see, for example, the currently available iSTAT™ test cartridges available from Abbott Point of Care Inc., Princeton, N.J.). In general, urease is deposited on the electrode and "held in place" by crosslinking into an insoluble form for entrapment in a polymer. A cover membrane is then typically applied to further retain the enzyme and provide protection from fouling, interferents, etc. However, problems have been encountered when attempting to adapt this technology to produce a multi-use BUN biosensor. A poor use-life has typically been observed for multi-use BUN biosensors; the poor use-life is the result of various factors that include (but are not limited to) an insufficient amount of active urease often being immobilized on the biosensor, performance degradation due to loss of urease from leeching over time, and use-based enzyme degradation.

DETAILED DESCRIPTION

Figure 1:
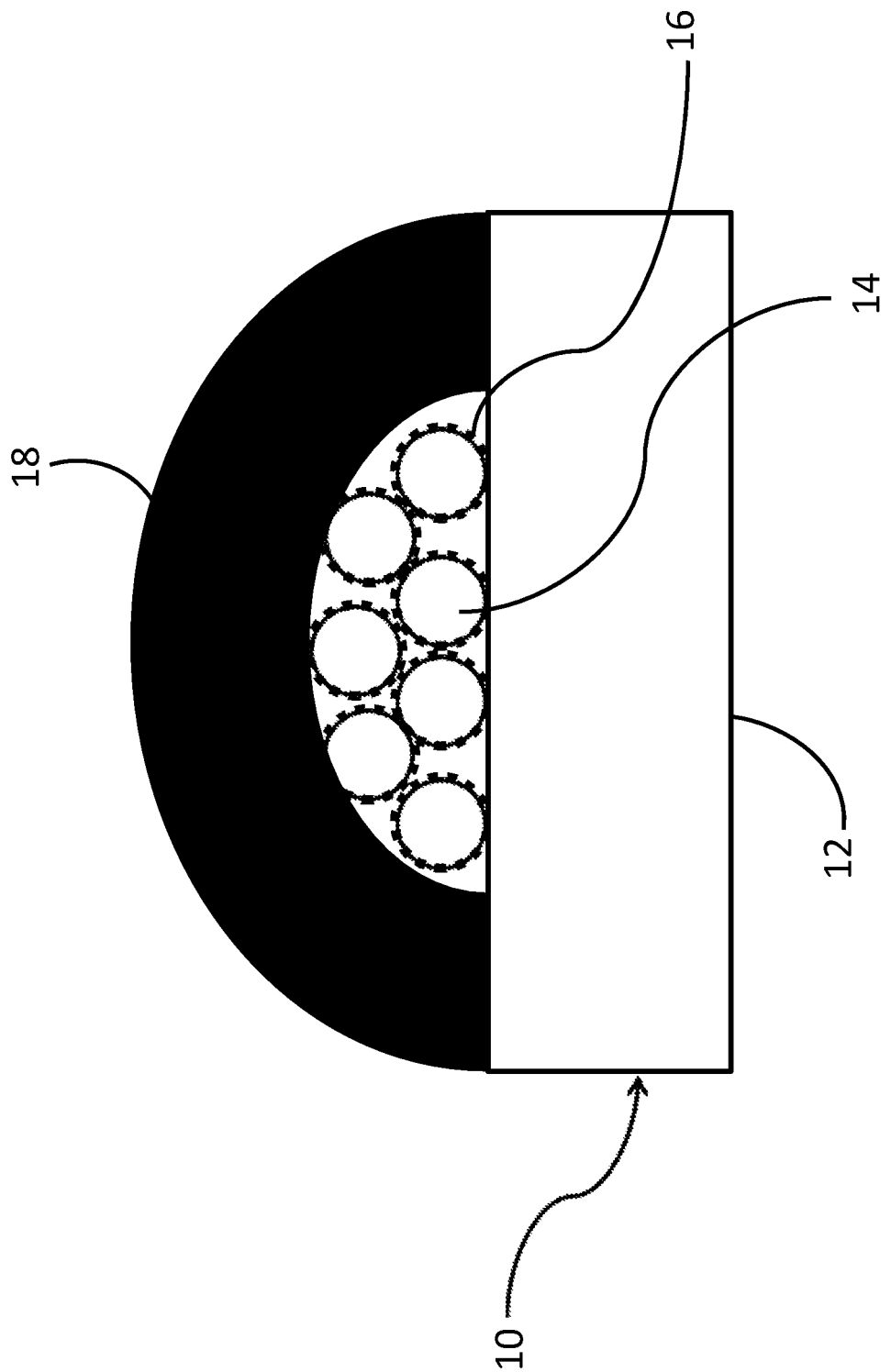
FIG. 1 is a pictorial representation of one non-limiting embodiment of a biosensor constructed in accordance with the inventive concepts disclosed herein.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which this presently disclosed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, and/or methods disclosed herein can be made and executed without undue experimentation in light of the present disclosure. While the articles, compositions, and methods of the inventive concept(s) have been described in terms of particular embodiments, it will be apparent to those of skill in the art that variations may be applied to the articles, compositions and/or methods and in the steps or in the sequence of steps of the methods described herein without departing from the concept, spirit and scope of the inventive concept(s). All such similar substitutes and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The term "about" is used to indicate that a value includes the inherent variation of error for the device, the method being employed to determine the value and/or the variation that exists among study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with" and "coupled to" include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

The term "sample" as used herein will be understood to include any type of biological sample that may be utilized in accordance with the presently disclosed inventive concept(s). Examples of fluidic biological samples that may be utilized include, but are not limited to, whole blood or any portion thereof (i.e., plasma or serum), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, combinations thereof, and the like.

The term "patient" includes human and veterinary subjects. In certain embodiments, a patient is a mammal. In certain other embodiments, the patient is a human. "Mammal" for purposes of treatment refers to any animal classified as a mammal, including human, domestic and farm animals, nonhuman primates, and zoo, sports, or pet animals, such as dogs, horses, cats, cows, etc.

The term "electrode" as used herein refers to any type of conductor or medium that is capable of functioning in accordance with the presently disclosed inventive concept(s). Non-limiting examples of electrodes that fall within the scope of the presently disclosed inventive concept(s) include electrochemical cells comprising a plurality of electrodes. Exemplary electrochemical cell constructs include a two-electrode cell comprising one indicator electrode and one reference electrode, a two-electrode cell comprising one anode and one cathode, a three-electrode cell comprising one anode, one cathode and one reference electrode, and a four-electrode cell comprising two working electrodes, one counter electrode, and one reference electrode.

Currently, multi-use biosensors are available for use in sensor arrays. However, these biosensors typically have a short use-life, generally due to insufficient active enzyme immobilized on the biosensor, degraded performance caused by the loss of the enzyme leaching over time, degradation of the enzyme simply due to use, and/or insufficient enzyme activity due to fouling and/or interferents.

Therefore, there is a need in the art for new and improved multi-use biosensors which solve the problems of the current multi-use biosensors of the prior art while also being able to be used in a sensor array assembly. In particular, there is a need in the art for multi-use biosensors (such as BUN and other enzyme-based biosensors) that possess at least a 14-day use-life (such as, but not limited to, at least a 30-day use-life) and a 3000 sample capability while substantially maintaining the integrity, response, and precision of the biosensor.

Turning now to the presently disclosed inventive concept(s), certain embodiments thereof are directed to a multi-use biosensor for detecting the presence and/or concentration of at least one target analyte in a fluidic biological sample. The multi-use biosensor comprises an electrode, a plurality of nanobeads having enzyme coupled thereto, and a semi-permeable membrane (also referred to herein interchangeably as a "cover membrane"). Each of the plurality of nanobeads has at least one enzyme coupled thereto; the enzyme interacts with the target analyte for detection of the target analyte. The plurality of nanobeads (with enzyme coupled thereto) is dispensed on the electrode, and the semi-permeable membrane is disposed on the plurality of the nanobeads, whereby the membrane immobilizes the plurality of nanobeads on the electrode. The membrane is permeable to the target analyte(s) to be detected but substantially impermeable to the enzyme coupled to the nanobeads.

The multi-use biosensor of the presently disclosed inventive concept(s) overcomes the defects and disadvantages of the prior art by attaching enzyme to nanobead rather than directly to the electrode, thereby providing the multi-use biosensor with an increased use-life and sample capability. For example (but not by way of limitation), the multi-use biosensor may substantially maintain the integrity thereof over a use-life of at least about 14 days and a sample capability of at least about 3000 samples.

Currently there are two general approaches utilized to produce multi-biosensor array products. In these approaches, the individual sensors are produced separately and then stitched together in an array after the chemistry has been performed on each sensor; alternatively, a single substrate is used that contains multiple electrodes in an array, and the appropriate coupling chemistry (e.g. enzyme attachment by crosslinking) is performed on each electrode (typically by dispensing reagents sequentially). This second option possesses the benefits of reduced cost and reduced sample volume; however, there is an increased risk that the whole array will be ruined if any issues arise in any one of the electrode chemistries during manufacturing.

Therefore, one of the defects of the standard crosslinking methods of the prior art is that the coupling chemistry is performed directly on the electrode during manufacture, and this direct interaction increases the risk and complexity of the manufacture, especially if there are multiple electrodes that on which one or more coupling chemistries are performed in a "single substrate" multi-sensor array product. The presently disclosed inventive concept(s) overcome this defect by performing the electrode chemistry external to the final array manufacturing process, thereby significantly reducing the risks associated with the manufacturing process. By coupling enzyme to nanobeads offline, the enzyme-nanobead conjugate can be validated (such as for activity, kinetics, etc.) before attachment to the electrode during manufacture—removing the need to crosslink the enzyme onboard the array.

Turning back to the particular components of the multi-use biosensor, any type of sensor known in the art as capable of use in a biosensor comprising an enzyme can be utilized in accordance with the presently disclosed inventive concept(s). For example (but not by way of limitation), the biosensor may be a potentiometric, amperometric, impedimetric, or conductometric sensor. In addition, any electrodes known in the art as capable of use with one of the above types of biosensors can be utilized in accordance with the presently disclosed inventive concept(s). Non-limiting examples of electrodes that may be utilized include ion-specific or ion-selective electrodes (ISE). The specific type of electrode selected will be dependent on the sensor type (i.e., potentiometric, amperometric, impedimetric, conductometric, etc.).

The electrode may possess any shape that allows the electrode to function in accordance with the presently disclosed inventive concept(s). For example, in certain non-limiting embodiments, the electrode may be planar or circular in shape. The electrode can be fabricated by any method known in the art or otherwise contemplated herein. Examples of fabrication methods that can be utilized in accordance with the presently disclosed inventive concept(s) include, but are not limited to, screen printing, metal sputtering, photolithography, or any other standard electrode manufacturing method.

The target analyte(s) may be any analyte present in a fluidic biological sample and that is known in the art or otherwise contemplated herein for detection by an enzyme-containing biosensor. Non-limiting examples of target analytes include blood urea nitrogen (BUN), glucose, glutamate, lactate, ethanol, ascorbic acid, choline acetylcholine, creatinine, cholesterol, pyruvate, bilirubin, and the like.

Any enzyme known in the art as capable of use in a biosensor for detection of a target analyte in a fluidic biological sample falls within the scope of the presently disclosed inventive concept(s). Non-limiting examples of enzymes include urease, glucose oxidase, glutamate oxidase, lactate oxidase, pyruvate oxidase, sarcosine oxidase, creatinine amidohydrolase, creatine amidinohydrolase, ascorbate oxidase, alcohol oxidase, cholesterol oxidase, choline oxidase, bilirubin oxidase, laccase, tyrosinase, alcohol dehydrogenase, glucose dehydrogenase, glutamate dehydrogenase, lactate dehydrogenase, pyruvate dehydrogenase, combinations thereof, and the like.

Any nanobeads known in the art and capable of functioning as described herein can be utilized in accordance with the presently disclosed inventive concept(s). It will be understood that the nanobeads can be formed of any suitable material appropriate for functioning as described or otherwise contemplated herein. In certain non-limiting embodiments, the nanobead is selected based on its surface (both the amount of surface area as well as the specific type of surface) and its compatibility and stability with the utilized enzyme. In certain particular embodiments, the nanobeads are formed of a non-magnetic material such as, but not limited to, latex.

In addition, the nanobeads are, in certain non-limiting embodiments, of a sufficient weight to minimize or prevent grouping (allows for dispersion) and have a diameter that provides sufficient surface area for coupling and immobilization of a sufficient concentration of the enzyme on the surface of each nanobead. In certain particular (but non-limiting) embodiments, the nanobeads may have a diameter of about 100 nm, about 125 nm, about 150 nm, about 175 nm, about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 675 nm, about 700 nm, about 725 nm, about 750 nm, about 775 nm, about 800 nm, about 825 nm, about 850 nm, about 875 nm, about 900 nm, about 925 nm, about 950 nm, about 975 nm, and about 1 µm. In addition, nanobeads having a diameter that falls within any range formed from the combination of two values listed above (for example, a range of from about 225 nm to about 850 nm, a range of from about 375 nm to about 675 nm, etc.) is also encompassed within the scope of the presently disclosed inventive concept(s). In a particular (but non-limiting embodiment), the nanobeads have a diameter in a range of from about 80 nm to about 1 µm.

In contrast, the size of the enzyme coupled to the nanobead will be substantially smaller than the diameter of the nanobead. For example (but not by way of limitation), the enzyme urease is about 15-20 nm in size, and certain enzymes utilized in accordance with the presently disclosed inventive concept(s) will be about 30 nm or less in size. Thus, the substantially smaller size of the enzyme compared to the nanobead will allow for the coupling of multiple enzymes per nanobead, thereby increasing the concentration of enzyme immobilized on the biosensor. In addition, the large size of the nanobead relative to the enzyme (in addition to the attachment of the enzyme to the nanobead) will prevent the enzyme from leeching out from the biosensor, thereby extending the biosensor's use-life.

Any covalent or non-covalent coupling mechanism known in the art or otherwise contemplated herein that is capable of coupling the enzyme to the nanobead may be utilized in accordance with the presently disclosed inventive concept(s). In certain non-limiting embodiments, the at least one enzyme may be coupled to each of the nanobeads via crosslinking. Any known crosslinking methods can be utilized in accordance with the presently disclosed inventive concept(s); for example (but not by way of limitation), one coupling chemistry that may be utilized is the avidin-biotin interaction, wherein the plurality of nanobeads are coated with streptavidin, while the at least one enzyme is conjugated to biotin.

In a particular (but non-limiting) example, the nanobeads are streptavidin-coated latex nanobeads such as (but not limited to) 294 nm POWER-BIND™ styrene/acrylic streptavidin-coated nanobeads (Thermo Fisher Scientific Inc., Waltham, Mass.).

Alternatively, the at least one enzyme may be covalently attached to the nanobeads. Any known covalent attachment methods can be utilized in accordance with the presently disclosed inventive concept(s); for example (but not by way of limitation), the at least one enzyme may be covalently attached to the nanobeads via a reactive group selected from the group comprising an aldehyde-, amine-, carbonyl-, carboxyl-, maleimide-, sulfhydryl-reactive group. Particular (but non-limiting) examples of covalent coupling technologies include COOH functionalized nanobeads and 1-ethyl-3-(-3-dimethylaminopropyl) carbodiimide hydrochloride ("EDC")/N-hydroxysuccinimide esters ("NHS") reactions.

The enzyme may be present on each nanobead at any percentage of surface area that allows the biosensor to perform in accordance with the presently disclosed inventive concept(s). For example (but not by way of limitation), the enzyme must be present on a sufficient amount of surface area of the nanobead to allow for sufficient capture of the target analyte by the biosensor. In certain particular (but non-limiting) embodiments, the enzyme may be present on each nanobead at a percent surface area of about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 99%. In addition, the scope of the presently disclosed inventive concept(s) also includes the presence of the enzyme on each nanobead at any percent surface area that falls within any range formed from the combination of two values listed above (for example, a range of from about 10% to about 95% surface area, a range of from about 40% to about 75% surface area, etc.).

Likewise, the nanobeads may be deposited on the electrode at any concentration that allows the biosensor to perform in accordance with the presently disclosed inventive concept(s). For example (but not by way of limitation), the nanobeads may be deposited on the electrode at a concentration that provides sufficient spacing between the nanobeads to allow for better washing and to prevent carryover between biological samples. In certain particular (but non-limiting) embodiments, the nanobeads may be present on the electrode at a percent surface area of about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 99%. In addition, the scope of the presently disclosed inventive concept(s) also includes the presence of the nanobeads on the electrode at any percentage of surface area that falls within any range formed from the combination of two values listed above (for example, a range of from about 10% to about 75% surface area, a range of from about 10% to about 50%, etc.).

In certain non-limiting embodiments, there is no physical attachment between the nanobeads and the electrode. Instead, the semi-permeable cover membrane is placed over the nanobeads (having the enzyme coupled thereto) to hold the nanobeads in place on the electrode. Cover membranes have previously been used as components of biosensors; non-limiting examples thereof that may be utilized in accordance with the presently disclosed inventive concept(s) are disclosed in U.S. Pat. No. 7,959,791 (the entire contents of which are hereby expressly incorporated herein by reference). Therefore, a person of ordinary skill in the art would be aware of cover membranes that can be utilized in accordance with the presently disclosed inventive concept(s), wherein the cover membrane is semi-permeable in order to allow passage of the biological analytes as well as removal of any byproduct.

The semi-permeable membrane may be formed of any material known in the art or otherwise contemplated herein that allows the biosensor to perform in accordance with the presently disclosed inventive concept(s). That is, the semi-permeable membrane must be formed of a material that is permeable to the target analyte(s) to be detected but is substantially impermeable to the enzyme coupled to the nanobeads. Non-limiting examples of materials from which the semi-permeable membrane can be formed include polyurethane, silicone, poly(vinyl chloride), combinations thereof, and the like. One particular (but non-limiting) example of a material from which the semi-permeable membrane can be constructed is HydroMed™ D7, a polyester based polyurethane (AdvanSource Biomaterials Corp., Wilmington, Mass.).

The semi-permeable membrane can be easily washed with a wash solution in between uses to remove any by-product. Prior to the use of nanobeads in the presently disclosed inventive concept(s), the dense crosslinked enzyme layer could retain the byproducts and cause carryover from earlier biological samples.

The coupling of enzyme to nanobead provides surprising and unexpected improvements over the prior art methods of coupling the enzyme directly to the biosensor. The use of nanobeads in accordance with the presently disclosed inventive concept(s) leads to a longer use-life for the biosensor while also maximizing the biosensor's response (and therefore also the precision of the biosensor). In addition, high loading of urease on the electrode is achieved due to the large surface area of the nanobeads; this high degree of loading serves to extend the biosensor's use-life while also maximizing precision of the biosensor. Also, a wide variety of well-known chemistries can be utilized to couple the enzyme to the nanobeads, and these coupling chemistries can be performed offline relative to the electrode dispensing and assembly of any biosensor arrays; in addition, the use of these coupling chemistries enables critical enzyme modifications to be performed offline during biosensor array manufacturing and thus leads to a longer use-life for the biosensor and also maximizes the response and precision of the biosensor. The nanobeads can be prepared and validated before any dispensing begins, thereby reducing the chance of a "bad" biosensor being created (i.e., by immobilizing an insufficient amount of active enzyme on the electrode) and thereby ruining the production of an entire biosensor array assembly. Good enzyme stability is also achieved by using the appropriate nanobead and nanobead surface. Further, the large size of the nanobeads relative to the enzyme coupled thereto prevents the leeching of the enzyme from the biosensor through the cover membrane, thereby extending use-life of the biosensor. The nanobeads also provide an efficient diffusional path for the target analyte(s) due to gaps formed in between nanobeads, and these spaces are observed even when the nanobeads are closely packed; as such, the kinetics and read time of the biosensor are increased, while sample carryover is decreased.

The presently disclosed inventive concept(s) eliminates the need to replace the biosensors after each use, or after several uses. Rather, the biosensors of the presently disclosed inventive concept(s) have an enhanced use-life, and can simply be washed with wash solution between uses. Moreover, the presently disclosed inventive concept(s) reduces carryover between biological samples because the spacing between the nanobeads allows for a better cleaning between biological sample runs. As such, the presently disclosed inventive concept(s) improves the prior art by reducing the amount of turnaround time (because multiple tests can be conducted at once) and reducing the amount of maintenance time spent on the instrumentation, such as blood gas analyzers.

Certain embodiments of the presently disclosed inventive concept(s) are directed to a multi-use biosensor array assembly that includes a plurality of the multi-use biosensors described in detail herein above, in combination with a substrate. At least two enzymes of each of the plurality of multi-use biosensors present in the multi-use biosensor array assembly are different from one another. In certain embodiments, all of the enzymes present in the array assembly may be different; alternatively, at least two enzymes of each of the plurality of multi-use biosensors present in the multi-use biosensor array assembly may be the same. The substrate has a first surface and a second surface opposite the first surface, and each of the plurality of multi-use biosensors are spatially positioned on at least one of the surfaces of the substrate.

Certain additional embodiments of the presently disclosed inventive concept(s) are directed to a method of producing any of the multi-use analyte biosensors described herein above, wherein the biosensor can be prepared and manufactured to provide a stable and qualified product. In the method, at least one enzyme is coupled to at least one nanobead by any of the methods described in detail herein above or otherwise known in the art, and a plurality of nanobeads having at least one enzyme coupled thereto is deposited on an electrode. A semi-permeable membrane is then disposed on the nanobeads (having enzyme coupled thereto) that are deposited on the electrode; in this manner, the membrane immobilizes the plurality of nanobeads on the electrode.

The method may also include the optional step of qualifying an activity of the enzyme (before and/or after deposition on the electrode). For example, once the enzyme is coupled to the nanobead and prior to deposition on the electrode, testing can be conducted to determine enzyme activity. Then, upon qualification thereof, a desired amount of enzyme-loaded nanobeads are dispensed onto the electrode and immobilized thereon via the membrane.

Further embodiments of the presently disclosed inventive concept(s) are directed to a method of producing a multi-use biosensor array assembly. In the method, a plurality of multi-use biosensors (each being a biosensor as described in detail herein above) are formed and spatially disposed on at least one surface of a substrate.

Yet further embodiments of the presently disclosed inventive concept(s) are directed to a method for detecting the presence and/or concentration of a target analyte in a fluidic biological sample. In the method, a fluidic biological sample is inserted into a blood gas, electrolyte, and/or metabolite instrument containing any of the multi-use biosensors described in detail herein above. The presence and/or concentration of the target analyte is then captured by the multi-use biosensor and reported by the instrument. For example (but not by way of limitation), target analyte ions disperse though the multi-use biosensor and bind to the corresponding enzyme present on the multi-use biosensor. At that time, the ion level can be measured by any of the various methods currently known in the art or otherwise contemplated herein (including, but not limited to, change in membrane potential or amperometry).

In addition, other embodiments of the presently disclosed inventive concept(s) are directed to a method for detecting the presence and/or concentration of a plurality of target analytes in a fluidic biological sample. In the method, a fluidic biological sample is inserted into a blood gas, electrolyte, and/or metabolite instrument containing any of the multi-use biosensor array assemblies described in detail herein above. The presence and/or concentration of a plurality of target analytes is then captured by the individual multi-use biosensors of the array assembly and reported by the instrument. Therefore, the presently disclosed inventive concept(s) envisions simultaneously obtaining measurements for multiple analytes from multiple multi-use biosensors.

In each of the above detection methods, the fluidic biological sample may be selected from the group comprising whole blood or any portion thereof (i.e., plasma or serum), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, and combinations thereof.

Turning now to the Drawings, FIG. 1 depicts a multi-use biosensor 10 constructed in accordance with the presently disclosed inventive concept(s). The biosensor 10 comprises an electrode 12; dispensed on the electrode 12 is a plurality of nanobeads 14, each of which has a plurality of enzymes 16 coupled thereto. The biosensor 10 also comprises a semi-permeable cover membrane 18 that is disposed on the plurality of nanobeads 14 having the enzymes 16 coupled thereto. The semi-permeable cover membrane 18 immobilizes the nanobeads 14 (having the enzymes 16 coupled thereto) on the electrode 12.

The nanobeads 14 having enzyme 16 coupled thereto may be prepared and validated prior to dispensing the nanobeads 14 on the electrode 12; thus the nanobeads 14 are generally made in advance of manufacturing the biosensor 10. The attachment of the enzyme 16 to the nanobead 14 prior to deposition on the electrode 12 is an improvement over the prior art direct deposition of enzyme on electrode; the enzyme 16 coupled to nanobead 14 can be qualified prior to dispensing on to the electrode 12. This ability leads to better results, and less errors, for the biosensor (by allowing for detection of inactive enzyme). This is particularly important where, as envisioned in the presently disclosed inventive concept(s), the individual biosensors will be placed in a multi-sensor array, and one non-working biosensor can negatively impact the entire array.

Figure 2:
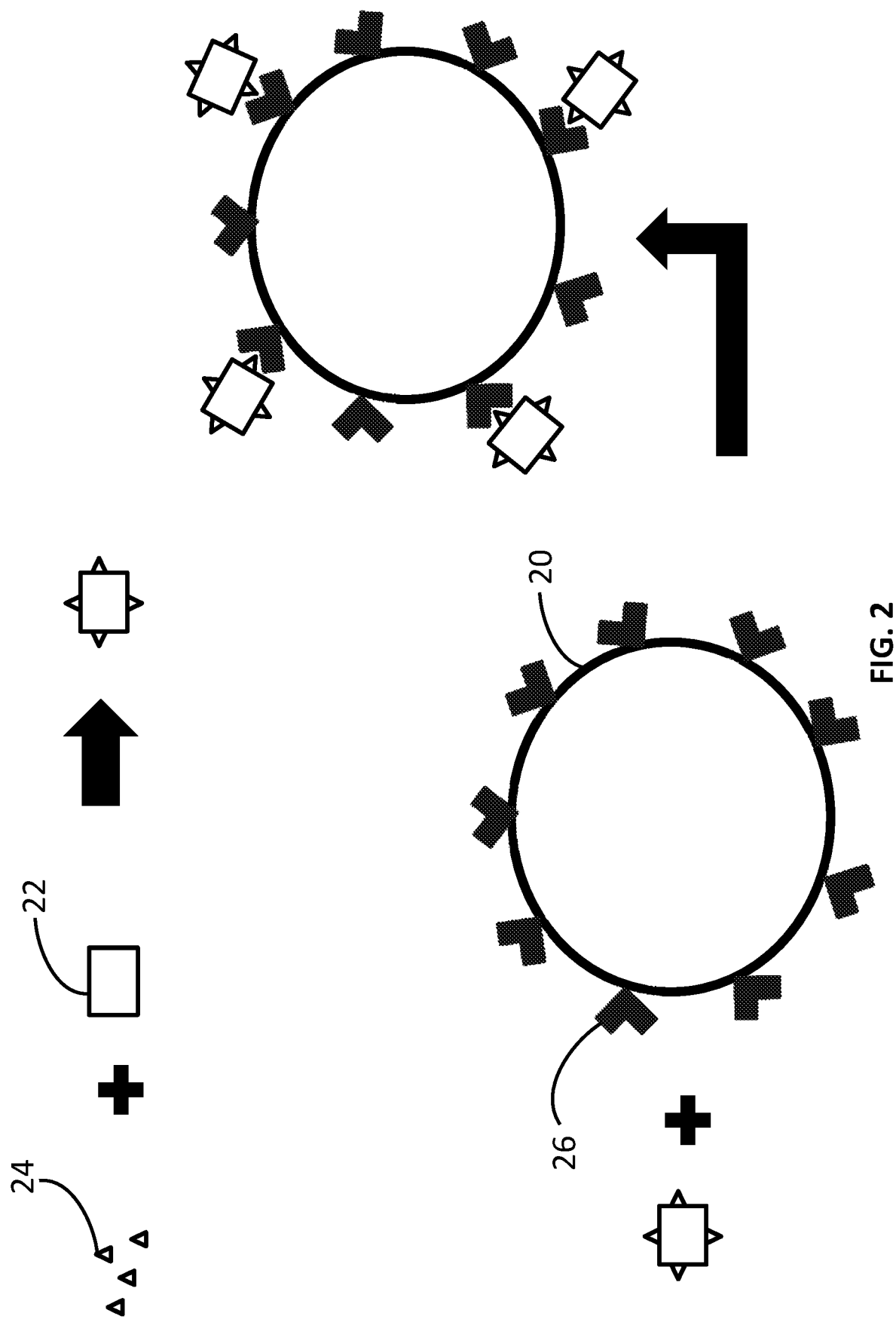
FIG. 2 is a pictorial representation of one non-limiting embodiment of crosslinking technology that may be used in conjunction with a nanobead constructed in accordance with the inventive concepts disclosed herein.

The enzyme can be conjugated to the nanobeads by any coupling mechanism described herein above or otherwise contemplated herein. For example (but not by way of limitation), FIG. 2 depicts one coupling mechanism that may be utilized in accordance with the presently disclosed inventive concept(s). In this embodiment, a nanobead 20 is coupled to a plurality of enzymes 22 through biotin-streptavidin crosslinking. The enzyme 22 is coated with biotin 24 and then reacted with the nanobead 20 coated with streptavidin 26.

Examples

An Example is provided hereinbelow. However, the presently disclosed inventive concept(s) is to be understood to not be limited in its application to the specific experimentation, results and laboratory procedures. Rather, the Examples are simply provided as one of various embodiments and are meant to be exemplary, not exhaustive.

In this particular example, the multi-use biosensor is a BUN biosensor (and thus the enzyme utilized is urease), and the avidin-biotin interaction is utilized to couple urease to the nanobead.

Materials and Methods

Urease (100 mg, BBI Solutions, Cardiff, UK) was dissolved in 1 ml 0.1M Phosphate Buffered Saline, pH 7.2 (PBS), and Sulfo-NHS-LC-LC-Biotin (0.6-2.8 mg, Thermo Fisher Scientific Inc., Waltham, Mass.) was added. After a two hour reaction at room temperature, excess biotin was removed from the mixture using a 7K MWCO Zeba column (Thermo Fisher Scientific Inc., Waltham, Mass.) using 0.1 M PBS as the eluent. The activity of the biotinylated enzyme was measured using standard urease assays.

Biotin-urease (10 mg) was added to 1 mg streptavidin-coated beads (294 nm POWER-BIND™ styrene/acrylic streptavidin-coated nanobeads, Thermo Fisher Scientific Inc., Waltham, Mass.). Optionally, excess enzyme was removed by repeated pelleting by centrifuge and washing of the beads using PBS.

The urease-beads (1 µl) were then dispensed onto a screen-printed Ag/AgCl electrode (1.5×0.5 mm) that contained a nonactin-based $NH_4^+$-sensing layer and allowed to dry (e.g. Butt and Cammann. (1992) *Anal. Lett.* 25:1597).

Next, a layer of HydroMed™ D7 polyurethane membrane (AdvanSource Biomaterials Corp., Wilmington, Mass.) was dispensed over the beads (2×0.5 µl, 4% in THF) and allowed to dry.

Finally, the potentiometric sensors were installed in a modified RAPIDPoint® 500 Blood Gas System (Siemens Medical Solutions USA, Inc., Malvern, Pa.) and continuously tested at 37° C. for a period of at least two weeks. At least 60 calibrator samples and 10 un-spiked blood samples were tested each day.

Results

Figure 3:
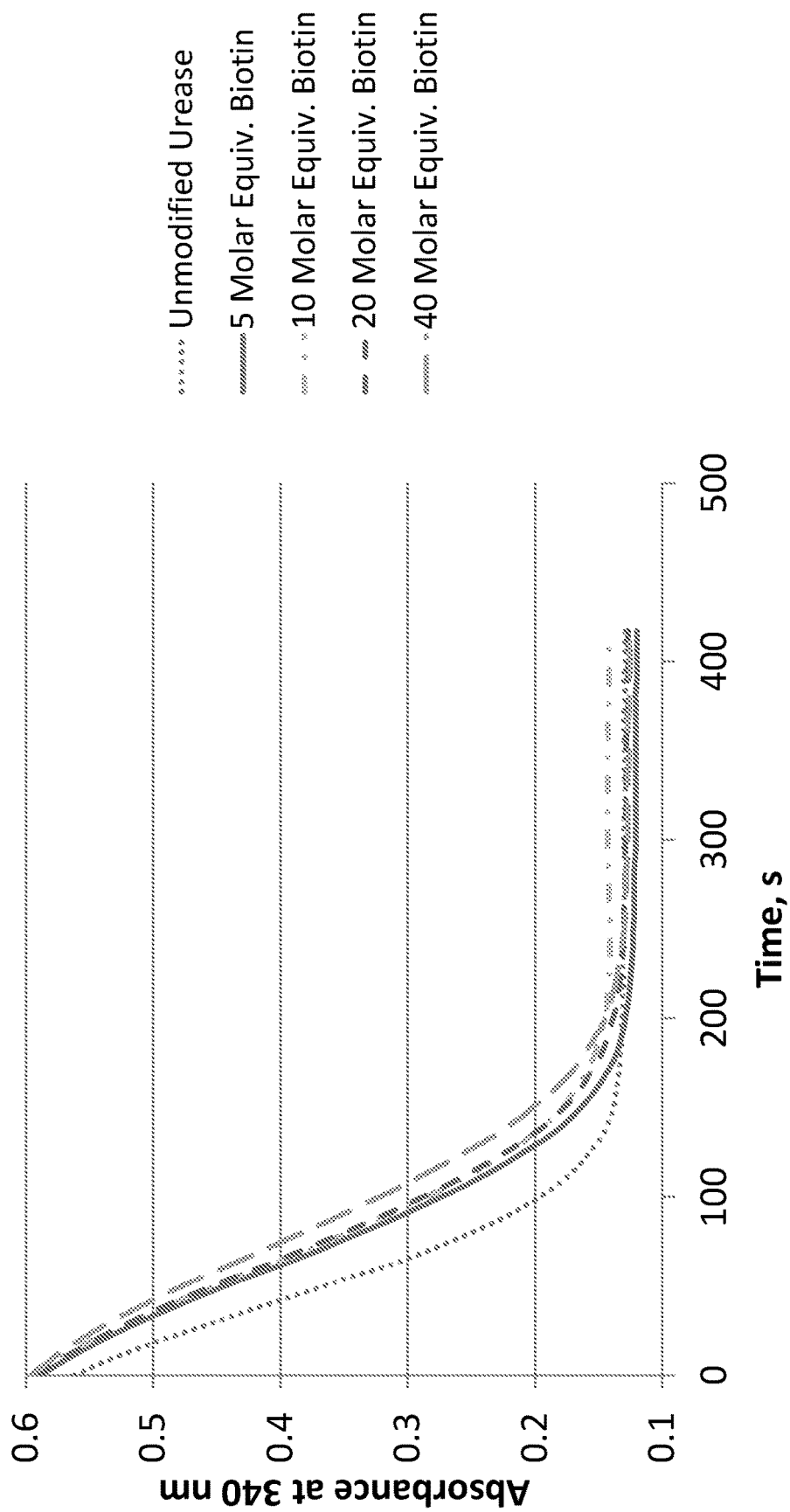
FIG. 3 is a graphical representation of the activity of biotinylated urease compared to unmodified urease; biotinylated urease is one non-limiting embodiment of a conjugate of enzyme to coupling mechanism for subsequent attachment to a nanobead for use in accordance with the presently disclosed inventive concept(s). This Figure demonstrates that urease can be biotinylated without significant loss of activity.

Urease was biotinylated using standard reagents such as Sulfo-NHS-LC-LC-Biotin (Thermo Fisher Scientific Inc., Waltham, Mass.). The level of biotinylation of urease was then maximized while maintaining enzyme activity; as shown in FIG. 3, the activity of urease was substantially maintained over a range of biotinylation levels, as measured using standard Glutamate Dehydrogenase/Aminate α-Ketoglutarate/Nicotinannide-Adenine Dinucleotide Assay (Worthington, CE. (1972) *Worthington Enzyme Manual*, Worthington Biochemical Corporation, Freehold, N.J.).

The biotinylated urease was then coupled to 294 nm POWER-BIND™ styrene/acrylic streptavidin-coated nanobeads (Thermo Fisher Scientific Inc., Waltham, Mass.), and the nanobeads (having urease coupled thereto) were dispensed onto a potentiometric electrode and immobilized thereon with a HydroMed™ D7 polyurethane membrane (AdvanSource Biomaterials Corp., Wilmington, Mass.).

Figure 4:
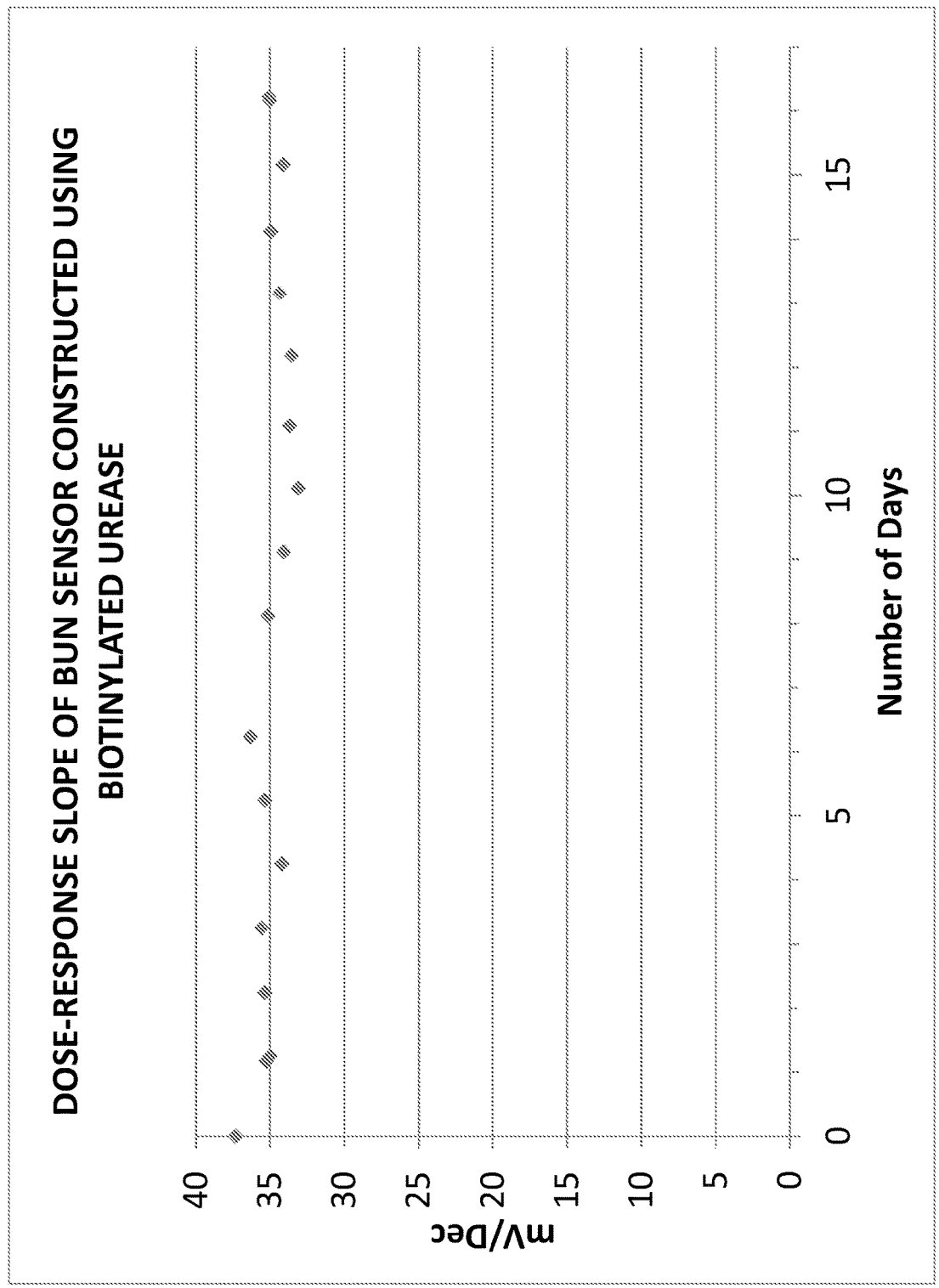
FIG. 4 is a graphical representation of the BUN assay dose-response slope associated with the multi-use biosensor constructed with the biotinylated urease of FIG. 3, in accordance with the presently disclosed inventive concept(s).
Figure 5:
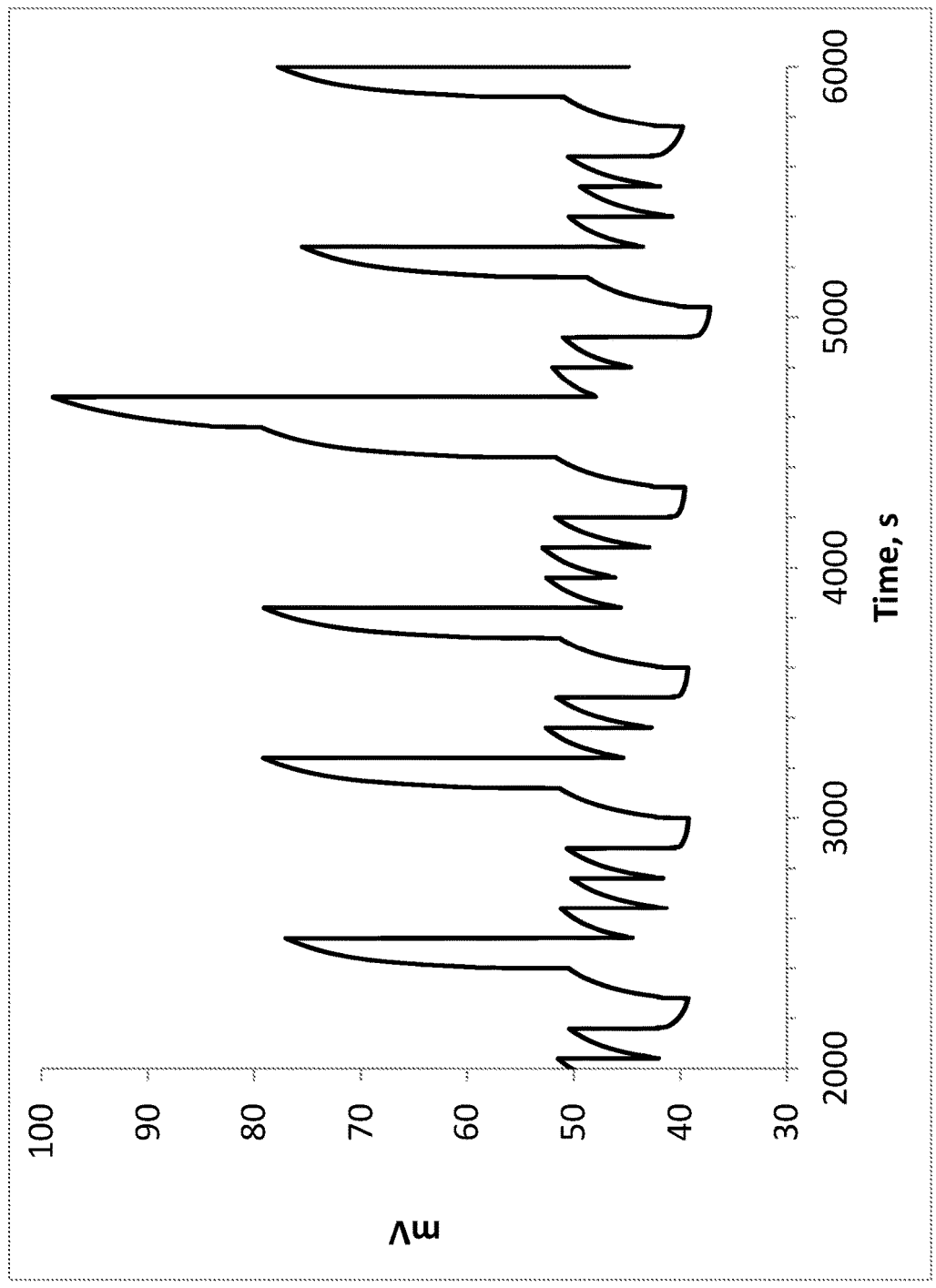
FIG. 5 is a graphical representation of the BUN assay response kinetics associated with the multi-use biosensor constructed with the biotinylated urease of FIG. 3, in accordance with the presently disclosed inventive concept(s).

FIGS. 4 and 5 show the assay dose-response slope and response kinetics of the sensor, respectively, to 1.8, 9.6, and 30 mM urea calibrator solutions. The sensors typically maintained full stability for at least two weeks.

Thus, in accordance with the presently disclosed inventive concept(s), there have been provided compositions and devices, as well as methods of producing and using same, which fully satisfy the objectives and advantages set forth hereinabove. Although the presently disclosed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed inventive concept(s).

Non-Limiting Embodiments of the Inventive Concept(s)

Certain embodiments are directed to a multi-use biosensor for detecting the presence and/or concentration of a target analyte in a fluidic biological sample. The multi-use biosensor comprises an electrode, a plurality of nanobeads, and a semi-permeable membrane. The plurality of nanobeads is dispensed on the electrode, and each of the plurality of nanobeads has at least one enzyme coupled thereto; the enzyme interacts with the target analyte for detection of the target analyte. The semi-permeable membrane is disposed on the plurality of the nanobeads, and the membrane immobilizes the plurality of nanobeads on the electrode. The membrane is permeable to the target analyte to be detected but substantially impermeable to the enzyme coupled to the nanobeads.

The multi-use biosensor may be a potentiometric analyte biosensor.

In certain embodiments, the at least one enzyme may be coupled to each of the nanobeads via crosslinking. For example, the plurality of nanobeads may be coated with streptavidin, and the at least one enzyme may be conjugated to biotin.

Alternatively, the at least one enzyme is covalently attached to the nanobeads. For example, the at least one enzyme may be covalently attached to the nanobeads via a reactive group selected from the group comprising an aldehyde-, amine-, carbonyl-, carboxyl-, maleimide-, and sulfhydryl-reactive group.

The plurality of nanobeads may have a diameter in a range of from about 100 nm to about 1 μm. In certain embodiments, the nanobeads are non-magnetic; for example, the nanobeads may comprise latex.

The semi-permeable membrane may be formed of a material selected from the group comprising polyurethane, silicone, poly(vinyl chloride), and combinations thereof.

In a particular, the multi-use biosensor may be further defined as a multi-use blood urea nitrogen (BUN) biosensor; in this instance, the at least one enzyme is urease.

The multi-use biosensor may have at least a 14 day use-life.

Certain embodiments are directed to a multi-use biosensor array assembly that includes a plurality of the multi-use biosensors described herein above, along with a substrate. The enzymes of at least two of the plurality of multi-use biosensors present in the multi-use biosensor array assembly are different. Each of the plurality of multi-use biosensors are spatially positioned on at least one surface of the substrate.

Certain embodiments are directed to a method of producing a multi-use analyte biosensor. The method comprises the steps of: (a) coupling at least one enzyme to at least one nanobead; (b) depositing a plurality of nanobeads having at least one enzyme coupled thereto on an electrode; and (c) disposing a semi-permeable membrane on the enzyme crosslinked nanobeads and electrode, wherein the membrane immobilizes the plurality of nanobeads on the electrode, and wherein the membrane is permeable to the analyte to be detected but substantially impermeable to the enzyme coupled to the nanobeads. The method may also include optional step (d) of qualifying an activity of the enzyme prior to step (b).

In the method, the multi-use analyte biosensor may be further defined as a potentiometric analyte biosensor.

In certain embodiments, step (a) is further defined as crosslinking the at least one enzyme to the least one nanobead. Alternatively, step (a) may be further defined as covalently attaching the at least one enzyme to the at least one nanobead.

The plurality of nanobeads may have a diameter in a range of from about 100 nm to about 1 μm. In certain embodiments, the nanobeads are non-magnetic; for example, the nanobeads may comprise latex.

The semi-permeable membrane may be formed of a material selected from the group comprising polyurethane, silicone, poly(vinyl chloride), and combinations thereof.

In a particular, the multi-use biosensor may be further defined as a multi-use blood urea nitrogen (BUN) biosensor; in this instance, the at least one enzyme is urease.

The multi-use biosensor may have at least a 14 day use-life.

Certain embodiments are also directed to a method of producing a multi-use biosensor array assembly. The method comprises the step of forming a plurality of multi-use biosensors on a first surface of a substrate (wherein each of the plurality of multi-use biosensors is formed as described in the embodiments above), wherein the enzymes of at least two of the plurality of multi-use biosensors are different, and wherein each of the plurality of multi-use biosensors are spatially positioned on at least one surface of the substrate.

Certain embodiments are also directed to a method for detecting the presence and/or concentration of a target analyte in a fluidic biological sample. The method comprises the steps of: (a) inserting a fluidic biological sample into a blood gas, electrolyte, and/or metabolite instrument containing any of the multi-use biosensors described in detail herein above; and (b) measuring the presence and/or concentration of the target analyte captured by the multi-use biosensor.

Certain embodiments are also directed to a method for detecting the presence and/or concentration of a plurality of target analytes in a fluidic biological sample. The method comprises the steps of: (a) inserting a fluidic biological sample into a blood gas, electrolyte, and/or metabolite instrument containing the multi-use biosensor array assembly described in detail herein above; and (b) measuring the presence and/or concentration of each of the plurality of target analytes captured by the individual multi-use biosensors of the array assembly.

In the above detection methods, the fluidic biological sample may be selected from the group comprising whole blood or any portion thereof (i.e., plasma or serum), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, and combinations thereof.

Below is a list of non-limiting, illustrative embodiments of the inventive concepts disclosed herein:

1. A multi-use biosensor for detecting the presence and/or concentration of a target analyte in a fluidic biological sample, the multi-use biosensor comprising: an electrode; a plurality of nanobeads dispensed on the electrode, wherein each of the plurality of nanobeads has at least one enzyme coupled thereto, wherein the enzyme interacts with the target analyte for detection of the target analyte; and a semipermeable membrane disposed on the plurality of the nanobeads, wherein the membrane immobilizes the plurality of nanobeads on the electrode, and wherein the membrane is permeable to the target analyte to be detected but substantially impermeable to the enzyme coupled to the nanobeads.

2. The multi-use biosensor of illustrative embodiment 1, further defined as a potentiometric analyte biosensor.

3. The multi-use biosensor of illustrative embodiment 1 or 2, wherein the at least one enzyme is coupled to each of the nanobeads via crosslinking.

4. The multi-use biosensor of illustrative embodiment 3, wherein the plurality of nanobeads are coated with streptavidin, and wherein the at least one enzyme is conjugated to biotin.

5. The multi-use biosensor of illustrative embodiment 1 or 2, wherein the at least one enzyme is covalently attached to the nanobeads.

6. The multi-use biosensor of illustrative embodiment 5, wherein the at least one enzyme is covalently attached to the nanobeads via a reactive group selected from the group comprising an aldehyde-, amine-, carbonyl-, carboxyl-, maleimide-, and sulfhydryl-reactive group.

7. The multi-use biosensor of any one of illustrative embodiments 1-6, wherein each of the plurality of nanobeads has a diameter in a range of from about 100 nm to about 1 μm.

8. The multi-use biosensor of any one of illustrative embodiments 1-7, wherein the nanobeads are non-magnetic.

9. The multi-use biosensor of any one of illustrative embodiments 1-8, wherein the nanobeads comprise latex.

10. The multi-use biosensor of any one of illustrative embodiments 1-9, wherein the semi-permeable membrane is formed of a material selected from the group comprising polyurethane, silicone, poly(vinyl chloride), and combinations thereof.

11. The multi-use biosensor of any one of illustrative embodiments 1-10, further defined as a multi-use blood urea nitrogen (BUN) biosensor, and wherein the at least one enzyme is urease.

12. The multi-use biosensor of any one of illustrative embodiments 1-11, wherein the biosensor has at least a 14 day use-life.

13. A multi-use biosensor array assembly, comprising: a substrate; a plurality of multi-use biosensors, each of the plurality of multi-use biosensors being a multi-use biosensor of any one of illustrative embodiments 1-12, wherein the enzymes of at least two of the plurality of multi-use biosensors are different, and wherein each of the plurality of multi-use biosensors are spatially positioned on at least one surface of the substrate.

14. A method of producing a multi-use analyte biosensor, the method comprising the steps of: (a) coupling at least one enzyme to at least one nanobead; (b) depositing a plurality of nanobeads having at least one enzyme coupled thereto on an electrode; and (c) disposing a semi-permeable membrane on the enzyme crosslinked nanobeads and electrode, wherein the membrane immobilizes the plurality of nanobeads on the electrode, and wherein the membrane is permeable to the analyte to be detected but substantially impermeable to the enzyme coupled to the nanobeads.

15. The method of illustrative embodiment 14, wherein the multi-use analyte biosensor is further defined as a potentiometric analyte biosensor.

16. The method of illustrative embodiment 14 or 15, wherein step (a) is further defined as crosslinking the at least one enzyme to the least one nanobead.

17. The method of illustrative embodiment 14 or 15, wherein step (a) is further defined as covalently attaching the at least one enzyme to the at least one nanobead.

18. The method of any one of illustrative embodiments 14-17, wherein each of the plurality of nanobeads has a diameter in a range of from about 100 nm to about 1 μm.

19. The method of any one of illustrative embodiments 14-18, wherein the nanobeads are non-magnetic.

20. The method of any one of illustrative embodiments 14-19, wherein the nanobeads comprise latex.

21. The method of any one of illustrative embodiments 14-20, wherein the semi-permeable membrane is formed of a material selected from the group comprising polyurethane, silicone, poly(vinyl chloride), and combinations thereof.

22. The method of any one of illustrative embodiments 14-21, wherein the biosensor is further defined as a multi-use blood urea nitrogen (BUN) biosensor, and wherein the at least one enzyme is urease.

23. The method of any one of illustrative embodiments 14-22, wherein the biosensor has at least a 14 day use-life.

24. The method of any one of illustrative embodiments 14-23, further comprising the step of: (d) qualifying an activity of the enzyme prior to step (b).

25. A method of producing a multi-use biosensor array assembly, the method comprising the step of: forming a plurality of multi-use biosensors on at least one surface of a substrate, wherein each of the plurality of multi-use biosensors is formed by the method of any one of illustrative embodiments 14-24, wherein the enzymes of at least two of the plurality of multi-use biosensors are different, and wherein each of the plurality of multi-use biosensors are spatially positioned on the at least one surface of the substrate.

26. A method for detecting the presence and/or concentration of a target analyte in a fluidic biological sample, the method comprising the steps of: (a) inserting a fluidic biological sample into a blood gas, electrolyte, and/or metabolite instrument containing the multi-use biosensor of any one of illustrative embodiments 1-12; and (b) measuring the presence and/or concentration of the target analyte captured by the multi-use biosensor.

27. A method for detecting the presence and/or concentration of a plurality of target analytes in a fluidic biological sample, the method comprising the steps of: (a) inserting a fluidic biological sample into a blood gas, electrolyte, and/or metabolite instrument containing the multi-use biosensor array assembly of illustrative embodiment 13; and (b) measuring the presence and/or concentration of each of the plurality of target analytes captured by the individual multi-use biosensors of the array assembly.

28. The method of illustrative embodiments 26 or 27, wherein the fluidic biological sample is selected from the group comprising blood, plasma, serum, urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, and combinations thereof.

What is claimed is:

1. A multi-use biosensor for detecting the presence and/or concentration of a target analyte in a fluidic biological sample, the multi-use biosensor comprising:
an electrode;
a plurality of nanobeads dispensed on the electrode, wherein each of the plurality of nanobeads has at least one enzyme coupled thereto via the plurality of nanobeads being coated with streptavidin and the at least one enzyme being conjugated to biotin, and wherein the enzyme interacts with the target analyte for detection of the target analyte; and a semi-permeable membrane disposed on the plurality of the nanobeads, wherein the membrane immobilizes the plurality of nanobeads on the electrode, and wherein the membrane is permeable to the target analyte to be detected but substantially impermeable to the enzyme coupled to the nanobeads.

2. The multi-use biosensor of claim 1, wherein the multi-use biosensor is a potentiometric analyte biosensor.

3. The multi-use biosensor of claim 1, wherein each of the plurality of nanobeads has a diameter in a range of from about 100 nm to about 1 μm.

4. The multi-use biosensor of claim 1, wherein the nanobeads are non-magnetic.

5. The multi-use biosensor of claim 1, wherein the nanobeads comprise latex.

6. The multi-use biosensor of claim 1, wherein the semi-permeable membrane is formed of a material selected from the group comprising polyurethane, silicone, poly(vinyl chloride), and combinations thereof.

7. The multi-use biosensor of claim 1, wherein the multi-use biosensor is a multi-use blood urea nitrogen (BUN) biosensor, and wherein the at least one enzyme is urease.

8. The multi-use biosensor of claim 1, wherein the biosensor has at least a 14 day use-life.

9. A multi-use biosensor array assembly, comprising:
a substrate;
a plurality of multi-use biosensors, each of the plurality of multi-use biosensors being a multi-use biosensor of claim 1, wherein the enzymes of at least two of the plurality of multi-use biosensors are different, and wherein each of the plurality of multi-use biosensors are spatially positioned on at least one surface of the substrate.

10. The multi-use biosensor array assembly of claim 9, wherein at least one of the plurality of multi-use biosensors is a multi-use blood urea nitrogen (BUN) biosensor, and wherein the at least one enzyme is urease.

11. A method for detecting the presence and/or concentration of a target analyte in a fluidic biological sample, the method comprising the steps of:
(a) inserting a fluidic biological sample into a blood gas, electrolyte, and/or metabolite instrument containing the multi-use biosensor of claim 1; and
(b) measuring the presence and/or concentration of the target analyte captured by the multi-use biosensor.

12. The method of claim 11, wherein the multi-use biosensor is a multi-use blood urea nitrogen (BUN) biosensor.

13. The method of claim 11, wherein the fluidic biological sample is selected from the group comprising blood, plasma, serum, urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, and combinations thereof.

14. A method for detecting the presence and/or concentration of a plurality of target analytes in a fluidic biological sample, the method comprising the steps of:
(a) inserting a fluidic biological sample into a blood gas, electrolyte, and/or metabolite instrument containing the multi-use biosensor array assembly of claim 9; and
(b) measuring the presence and/or concentration of each of the plurality of target analytes captured by the individual multi-use biosensors of the array assembly.

15. The method of claim 14, wherein at least one of the multi-use biosensors of the multi-use biosensor array assembly is a multi-use blood urea nitrogen (BUN) biosensor.

16. The method of claim 14, wherein the fluidic biological sample is selected from the group comprising blood, plasma, serum, urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, and combinations thereof.

17. A method of producing a multi-use analyte biosensor, the method comprising the steps of:
(a) coupling at least one enzyme to at least one nanobead via the at least one nanobead being coated with streptavidin and the at least one enzyme being conjugated to biotin;
(b) depositing a plurality of nanobeads having at least one enzyme coupled thereto on an electrode; and
(c) disposing a semi-permeable membrane on the enzyme crosslinked nanobeads and electrode, wherein the membrane immobilizes the plurality of nanobeads on the electrode, and wherein the membrane is permeable to the analyte to be detected but substantially impermeable to the enzyme coupled to the nanobeads.

18. The method of claim 17, wherein the multi-use analyte biosensor is a potentiometric analyte biosensor.

19. The method of claim 17, wherein each of the plurality of nanobeads has a diameter in a range of from about 100 nm to about 1 μm.

20. The method of claim 17, wherein the nanobeads are non-magnetic.

21. The method of claim 17, wherein the nanobeads comprise latex.

22. The method of claim 17, wherein the semi-permeable membrane is formed of a material selected from the group comprising polyurethane, silicone, poly(vinyl chloride), and combinations thereof.

23. The method of claim 17, wherein the biosensor is a multi-use blood urea nitrogen (BUN) biosensor, and wherein the at least one enzyme is urease.

24. The method of claim 17, wherein the biosensor has at least a 14 day use-life.

25. The method of claim 17, further comprising the step of:
(d) determining an activity of the enzyme prior to step (b).

26. A method of producing a multi-use biosensor array assembly, the method comprising the step of:
forming a plurality of multi-use biosensors on at least one surface of a substrate, wherein each of the plurality of multi-use biosensors is formed by the method of claim 17, wherein the enzymes of at least two of the plurality of multi-use biosensors are different, and wherein each of the plurality of multi-use biosensors are spatially positioned on the at least one surface of the substrate.

27. The method of claim 26, wherein at least one of the multi-use biosensors is a multi-use blood urea nitrogen (BUN) biosensor, and wherein the at least one enzyme is urease.

* * * * *